(12) United States Patent
Nakakado et al.

(10) Patent No.: US 6,748,996 B2
(45) Date of Patent: Jun. 15, 2004

(54) ROTATION DEVICE, METHOD FOR TRANSFERRING WORN ARTICLE, METHOD FOR FOLDING WEB, DEVICE FOR FOLDING WEB, AND DISPOSABLE WORN ARTICLE

(75) Inventors: Masaki Nakakado, Osaka (JP); Yuzo Ichiura, Osaka (JP); Satoshi Tanaka, Osaka (JP); Ikuo Tachibana, Hyogo (JP)

(73) Assignee: Zuiko Corporation, Osaka (JP)

( * ) Notice: Subject to any disclaimer, the term of this patent is extended or adjusted under 35 U.S.C. 154(b) by 218 days.

(21) Appl. No.: 09/995,053

(22) Filed: Nov. 27, 2001

(65) Prior Publication Data

US 2002/0103468 A1 Aug. 1, 2002

(30) Foreign Application Priority Data

Dec. 1, 2000 (JP) ........................ 2000-366782
Mar. 23, 2001 (JP) ........................ 2001-085164

(51) Int. Cl.[7] .................. A61F 13/15; B65H 20/16; B65H 45/14
(52) U.S. Cl. ................. 156/556; 156/566; 156/567; 156/494; 156/495; 414/754; 414/777; 414/783
(58) Field of Search ................. 156/556, 567, 156/566, 163, 164, 229, 494, 495, 496; 414/754, 777, 783

(56) References Cited

U.S. PATENT DOCUMENTS

| | | | |
|---|---|---|---|
| 4,506,779 A | 3/1985 | Seragnoli | |
| 4,578,133 A | * 3/1986 | Oshefsky et al. | 156/164 |
| 4,610,751 A | 9/1986 | Eschler | |
| 4,726,876 A | * 2/1988 | Tomsovic, Jr. | 156/552 |
| 4,767,487 A | 8/1988 | Tomsovic, Jr. | |
| 4,880,102 A | 11/1989 | Indrebo | |
| 5,025,910 A | 6/1991 | Lasure et al. | |
| 5,660,657 A | 8/1997 | Rajala et al. | |
| 6,022,443 A | 2/2000 | Rajala et al. | |

FOREIGN PATENT DOCUMENTS

| | | |
|---|---|---|
| EP | 0 805 116 A1 | 11/1997 |
| EP | 0 974 323 A1 | 1/2000 |
| GB | 2 214 202 a | 8/1989 |
| JP | 63317576 | 12/1988 |
| JP | 1272803 | 10/1989 |
| WO | WO 98/00356 | 1/1998 |

OTHER PUBLICATIONS

European Search Report, Jun. 20, 2002, one page.
THK LM System, R Guide HCR Type, THK Co., Ltd., Catalog No. 154–2, Publication Date Nov. 10, 1996, 4 pages.
THK LM System, General Catalog (No. 300–6), THK Co., Ltd., Publication Date Apr. 30, 2000, 3 pages.
NB Slide Way, Gonio Way RV Type (No. 4010), Nippon Bearing Co., Ltd., Publication Date May 5, 2000, 4 pages.

\* cited by examiner

*Primary Examiner*—Jeff H. Aftergut
(74) *Attorney, Agent, or Firm*—Eschweiler & Associates, LLC

(57) ABSTRACT

A rotation device includes: an endless guide; and a plurality of moving sections that move while being guided by the guide, wherein an interval between the moving sections can be changed.

9 Claims, 16 Drawing Sheets

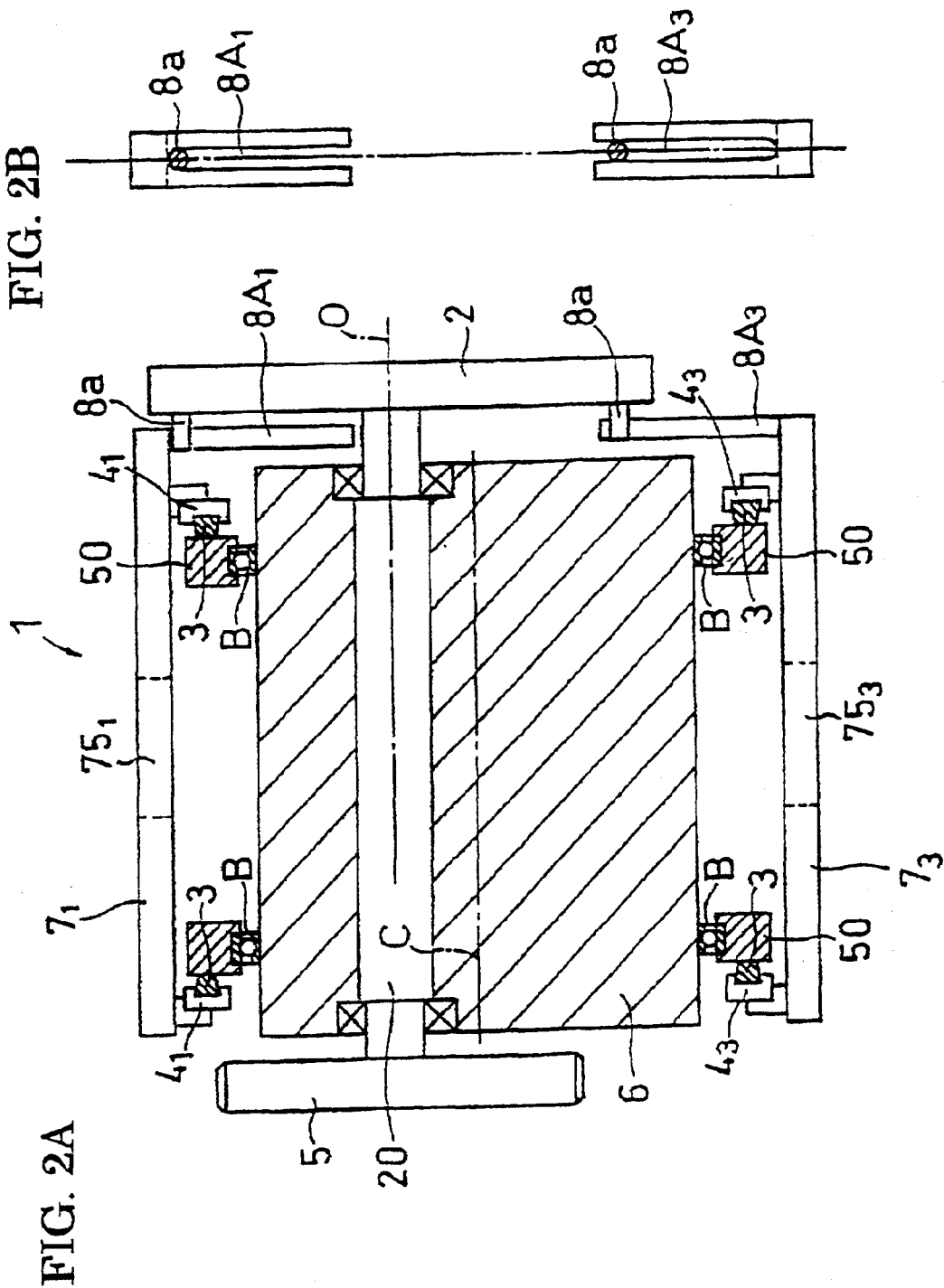

ROTATION DEVICE, METHOD FOR TRANSFERRING WORN ARTICLE, METHOD FOR FOLDING WEB, DEVICE FOR FOLDING WEB, AND DISPOSABLE WORN ARTICLE

BACKGROUND OF THE INVENTION

1. Field of the Invention

The present invention relates to a rotation device, a method for transferring a worn article, and a method for folding a web.

2. Background of the Invention

Japanese Laid-Open Patent Publication No. 63-317576, for example, discloses a movement of a plurality of pads rotating about a predetermined axis while each of the pads changes its velocity, during a process of producing a worn article or a web (a continuous material). Japanese National Phase PCT Laid-Open Publication No. 2000-514024 discloses a material engagement member reciprocating in a direction parallel to a rotation axis of a drum.

When each of the pads is supported by a bearing, the same number of bearings as the number of pads are required so that the velocities of the pads can be changed individually, thereby increasing the size and/or complexity of the device.

SUMMARY OF THE INVENTION

In view of the problem in the prior art, it is an object of the present invention to provide a rotation device having a simple structure and being capable of providing a complicated movement. It is also an object of the present invention to provide a method for transferring a worn article, a method for folding a web and a device for folding a web that can suitably employ the rotation device, and a disposable worn article produced by using the same.

In order to achieve the objects set forth above, a first rotation device of the present invention includes: an endless guide; a plurality of moving sections that slide while being guided by the guide; and a rotation member that allows the guide to rotate about an axis. In addition, the plurality of moving sections are arranged in the rotation allowance direction of the rotation member; and the plurality of moving sections can slide in the direction of rotation of the rotation member or in the opposite direction by being guided by the guide.

A second rotation device of the present invention includes: a plurality of guides; a plurality of moving sections that slide while being guided by the plurality of guides; and a rotation member that allows the plurality of guides to rotate about an axis. Furthermore each of the moving sections is guided by at least one of the guides; and the plurality of guides is provided about the axis so as to be arranged in the rotation allowance direction of the rotation member while surrounding the axis, so that the plurality of moving sections can slide in the direction of rotation of the rotation member or the opposite direction.

As a rotational force having a predetermined velocity curve is applied to the moving sections, the rotation member rotates at a high velocity along with the rotation of the moving sections. Meanwhile, each moving section rotates with respect to the guide at a low relative velocity. In this way, the friction between the moving sections and the guide is significantly reduced, thereby improving the durability of the device.

Ideally, the rotation member is capable of an unlimited rotation, and may be a ball bearing or a roller bearing including a rolling element such as a ball or a roller.

The guide may be any type of guide as long as it allows the sliding movement of the moving sections in a direction including a component of the rotation allowance direction of the rotation member. The term "endless guide" as used herein refers to not only a generally completely ring-shaped guide, but also to those having slight gaps in the circumferential direction, or even to those obtained by arranging guide elements, which together form one guide, so as to be spaced apart from one another at a predetermined interval. Moreover, the guide elements may overlap with one another as viewed in the axial direction. The phrase "in a direction including a component of the rotation allowance direction of the rotation member" as used herein means that a guide element may be provided in an inclined direction. The guide element may be a rail or a groove.

In the second rotation device of the present invention, the phrase "a plurality of guides" means that the guides are spaced apart from one another in the direction of rotation or in the axial direction to such a degree that a moving section cannot move from one guide to another.

Where one moving section moves from one of a plurality of guide elements to another, the plurality of guide elements together form one guide.

In the present invention, it is preferred to provide a controller for controlling the moving velocity of the moving sections. Such a controller causes the moving sections to rotate at differing predetermined instantaneous velocities, thereby changing the pitch between the moving sections during rotation.

The term "instantaneous velocity" as used herein refers to a velocity in a minute period of time, meaning that each moving section rotates while changing its velocity depending on the rotational position thereof.

The present invention can be used with a rotation device as described in PCT International Publication WO01/44086, a method for transferring worn articles while changing the pitch thereof, a method for folding a web, or a device for folding a web.

A method for folding a web of the present invention is a method for folding a web by using a rotation device including a plurality of pads that rotate about a predetermined axis so as to continuously transfer the web. The method includes: supplying the web onto surfaces of the rotation device pads; rotating adjacent ones of the pads onto which the web has been supplied so as to change the interval therebetween to slacken a portion of the web between the adjacent pads, thereby folding the portion of the web; and releasing the web from the pads.

Such a folding method can be realized using the first or second rotation devices of the present invention. Other rotation devices such as that described in PCT International Publication WO01/44086 may be used in place of the rotation device including a plurality of pads.

A device for folding a web of the present invention is a device for folding a web to form a wall in a direction transverse to a web running direction. The device includes: a transfer member for forming a slack portion in the web in the running direction thereof while continuously transferring the web; and a member for folding the slack portion so as to form the wall.

The term "wall" as used in the present invention refers to a portion of a web or a sheet-like material that has been folded, regardless of whether the wall is laid down along the surface of the web or standing on the web.

In the folding device of the present invention, the "transfer member" may be any member including a plurality of transfer sections for transferring the web in the web running direction, wherein the transfer velocity of one of the transfer sections is set to be lower than that of another transfer section upstream of the one of the transfer sections so as to form a slack portion in a portion of the web between the upstream and downstream transfer sections.

In the present invention, it is preferred to provide a directioning member for defining the direction in which a slack portion is to be folded.

In the present invention, the term "slack portion" refers to a portion of a web on which no tension is applied.

In the present invention, it is preferred to provide a fold-holding section for maintaining the shape or condition of a folded portion obtained by folding the slack portion.

BRIEF DESCRIPTION OF THE DRAWINGS

FIG. 2A is a schematic cross-sectional view illustrating a second embodiment of the rotation device of the present invention.

FIG. 2B is a side view illustrating a portion of a fixed pin and groove arrangement for controlling a rotational velocity of a bridging section according to the second embodiment of the invention.

DESCRIPTION OF THE PREFERRED EMBODIMENTS

Embodiments of the present invention will now be described with reference to the drawings.

Figure 1B:
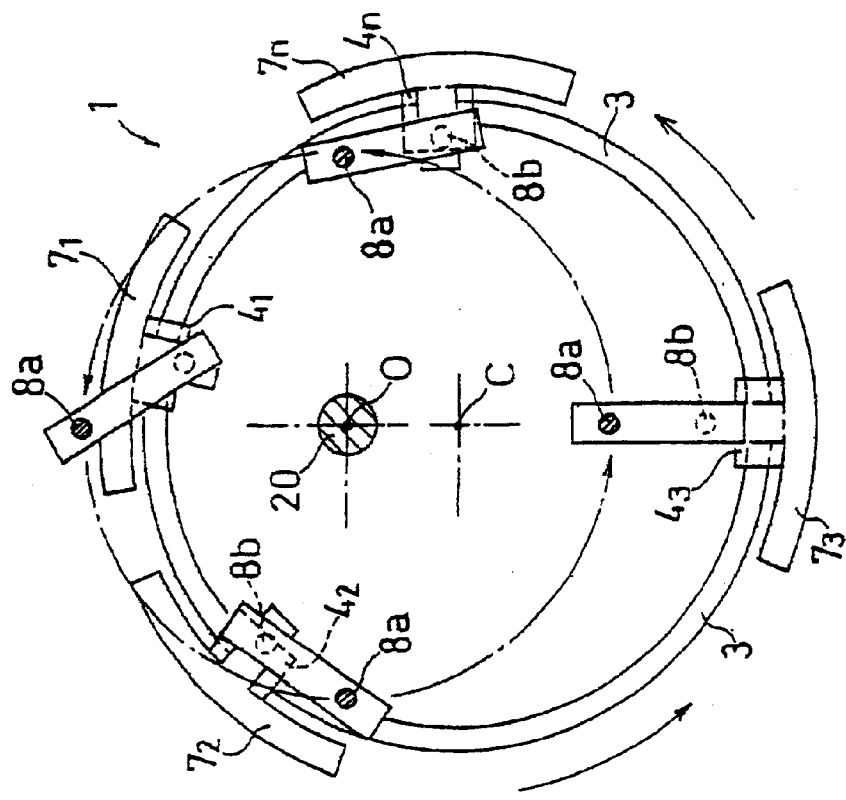
FIG. 1B is a side view illustrating the first embodiment of the rotation device of the present invention.
Figure 1A:
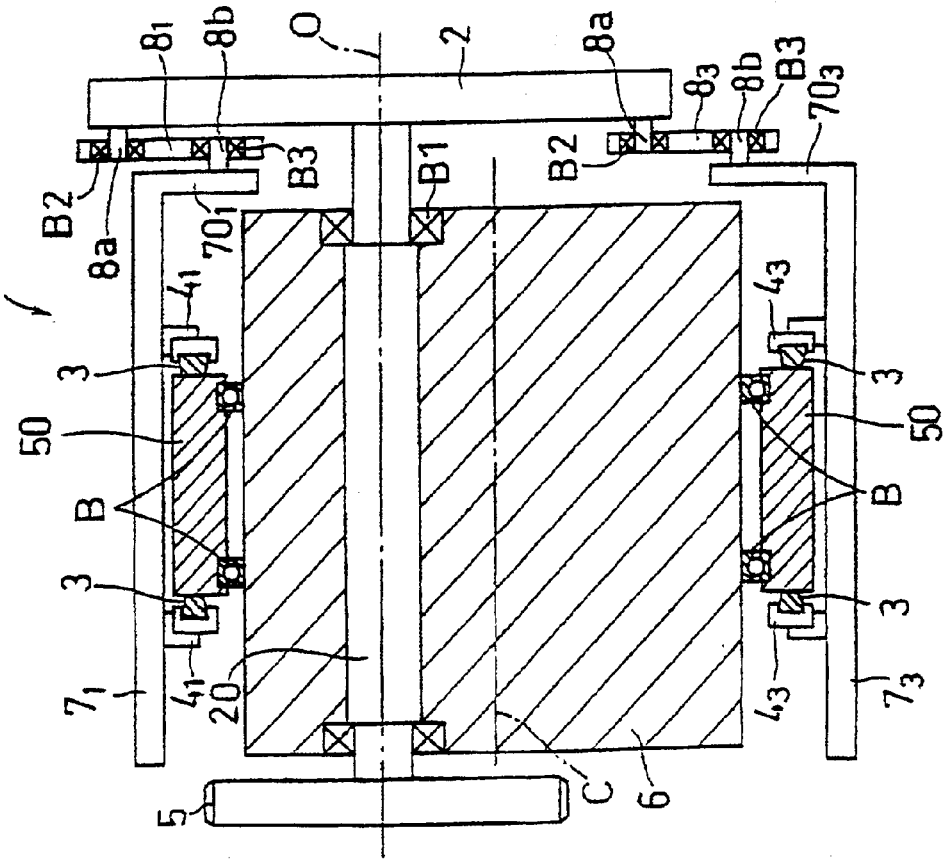
FIG. 1A is a schematic cross-sectional view illustrating a first embodiment of the rotation device of the present invention.

FIG. 1A and FIG. 1B illustrate a first embodiment of the present invention.

A rotation device 1 includes a rotation section B, a guide 3 and a plurality of moving sections $4_1$ to $4_n$. In the present embodiment, the rotation device 1 also includes a driving section 2.

The driving section 2 inputs a rotational force to the moving sections $4_i$. A rotational force from a rotational power source such as a motor is transmitted to the driving section 2 via a power transmission portion 5 and a shaft 20, so that the driving section 2 rotates about an axis O at a constant velocity, for example. The driving section 2 is axially and rotatably supported by a drum 6 via a bearing B1. The axis O of the driving section 2 is eccentric to an axis C of the drum 6. Due to such an eccentric structure, it is possible to, for example, periodically change the velocity of each moving section $4_i$ while the driving section 2 rotates.

A guide 3 is attached to the drum 6 via the rotation section B such as a ball bearing and a rotation ring 50. In the rotation device 1 illustrated in FIG. 1A, two or more endless guides 3 are provided spaced apart from each other in the axial direction of the drum 6. As shown in FIG. 1B, a plurality of moving sections $4_1$ to $4_i$ are attached to each guide 3 so that the moving sections $4_1$ to $4_i$ are movable in the circumferential direction of the guide 3. Therefore, each moving section $4_i$ rotates around the drum 6 along with the guide 3 while additionally moving relative to the guide 3 around the drum 6 along the guide 3.

Figure 6A:
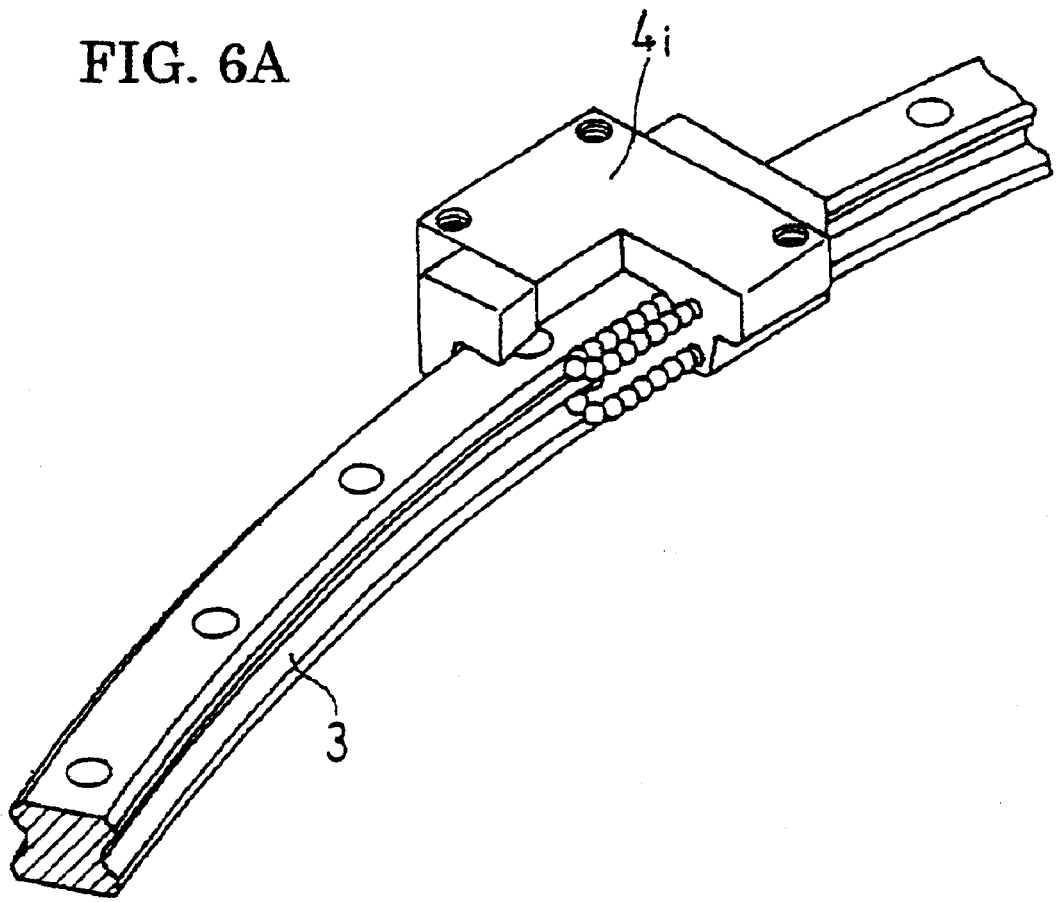
FIG. 6A is a perspective view illustrating an example of a guide and a moving section.
Figure 6B:
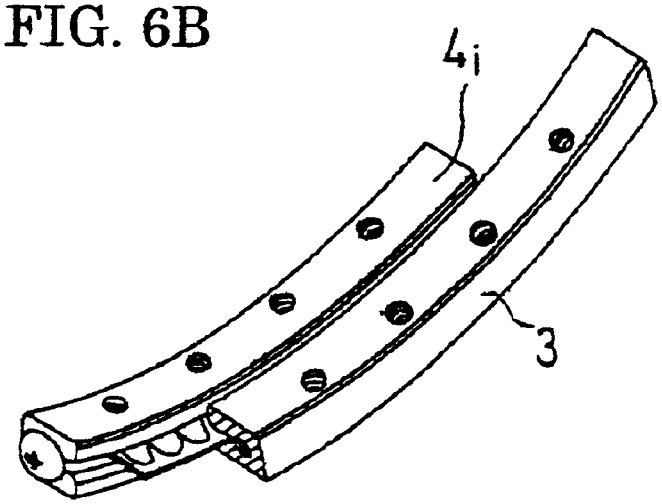
FIG. 6B is a perspective view illustrating another example of a guide and a moving section.

For the guide 3 and the moving section $4_i$, an R Guide manufactured by THK® Co., Ltd., as illustrated in FIG. 6A, or a Gonio Way manufactured by Nippon Bearing Co., Ltd., may suitably be employed. Preferably, a rolling element such as a ball or a wheel is inserted between the guide 3 and the moving section $4_i$. Each guide 3 may be a number of rails or grooves attached together in the circumferential direction of the rotation section B. Basically, it is preferred that the reciprocating movement is a rolling movement of a bearing, or the like, but may alternatively be a sliding movement.

In FIG. 1A, a bridging section $7_i$ is provided so as to extend between each pair of moving sections $4_i$ that are spaced apart from each other in the axial direction of the drum 6. One end of an arm $70_i$ is fixed to the bridging section $7_i$, and a link $8i$ is rotatably attached to the other end of the arm $70_i$.

In the present embodiment, a controller, being capable of moving the moving sections $4i$ at a programmed velocity, is provided by the link 8*i* in combination with the eccentricity between the axes C and O. Alternatively, the controller may be provided by any other link mechanism, or a controller described in PCT International Publication WO01/44086, for example, may be used.

One end of each link 8*i* is rotatably attached to the driving section 2 via a bearing B2 and a fixed pin 8*a*, and the other end of each link 8*i* is rotatably attached to the arm 70*i* via a bearing B3 and a rotation pin 8*b*. As the driving section 2 rotates at a substantially constant velocity, the fixed pin 8*a* rotates, together with the driving section 2, at a substantially constant angular velocity, while the rotation pin 8*b* rotates around the fixed pin 8*a*. Thus, the angular velocity of the rotation pin 8*b* changes depending on the rotation angle of the rotation pin 8*b*. Therefore, the bridging section 7*i* integral with the rotation pin 8*b* rotates around the drum 6 while changing the interval (pitch) with respect to an adjacent bridging section 7*j*, as illustrated in FIG. 1B.

Specifically, each bridging section 7*i* rotates at a relatively low velocity while it rotates from the position of the bridging section 7*n* to that of the bridging section 7$_2$ of FIG. 1B, whereas the bridging section 7*i* rotates at a higher velocity while it rotates from the position of the bridging section 7$_2$ to that of the bridging section 7*n*. Therefore, the spacing interval (pitch) between adjacent bridging sections 7*i* changes along with the rotation of the bridging sections 7*i*.

FIG. 2A and FIG. 2B illustrate a second embodiment of the rotation device 1.

In the present embodiment, the rotation ring 50 is coupled to each rotation section B, and an attachment section 75*i*, through which a pad to be described later is inserted, is provided in a generally central portion of each bridging section 7*i*. The attachment section 75*i* may be a space in the form of a through hole, a notch, a depression, etc.

Moreover, in the present embodiment, a groove 8A*i* elongated in the radial direction of the drum 6 is provided, instead of the link 8*i*, at an end of each bridging section 7*i*. The groove 8A*i* is provided with the fixed pin 8*a* illustrated in FIG. 2B so that the fixed pin 8*a* is slidable in the radial direction. Therefore, the rotational velocity of the bridging section 7*i* changes as in the first embodiment.

In the rotation device of FIG. 2A and FIG. 2B, the velocity of the bridging section 7*i* may be controlled by a link as illustrated in FIG. 1, or alternatively by any other controller mechanism as described above.

Figure 3A:
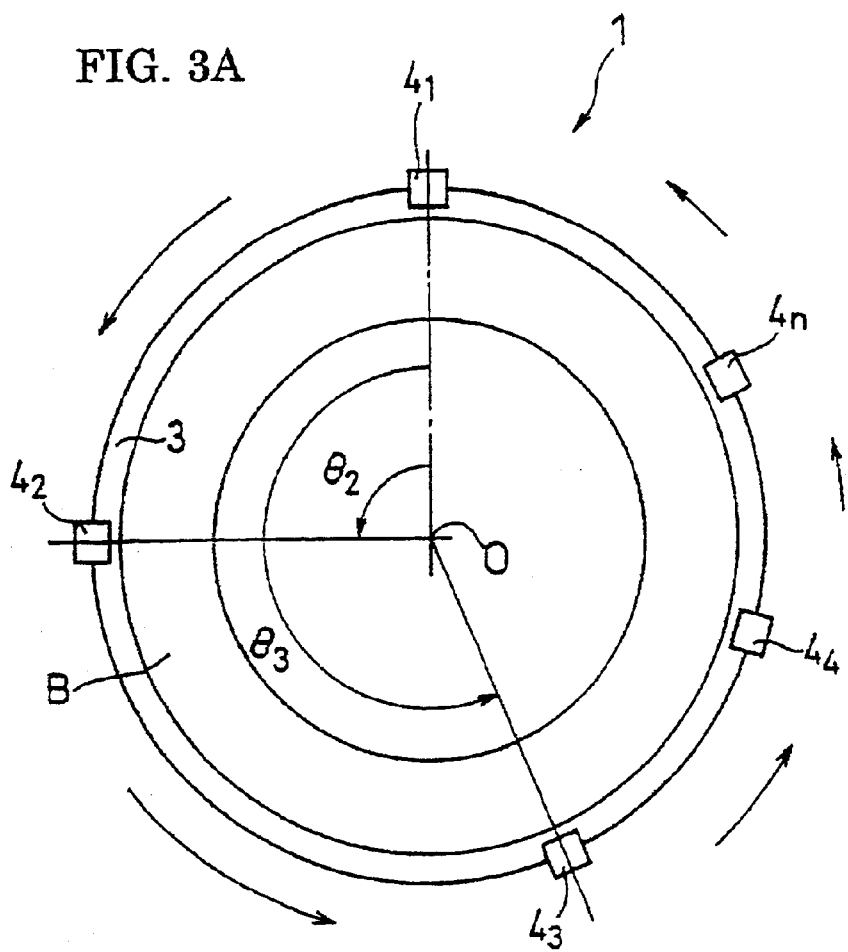
FIG. 3A is a schematic cross-sectional view illustrating a third embodiment of the rotation device of the present invention.
Figure 3B:
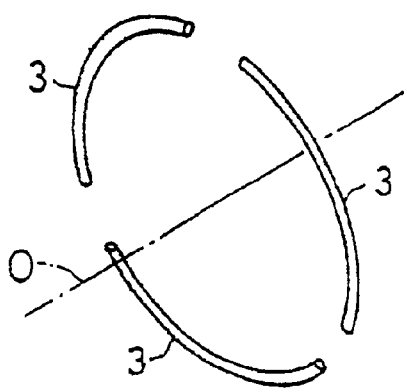
FIG. 3B is a schematic perspective view illustrating an example where a plurality of guides are provided in a concentric manner.
Figure 3C:
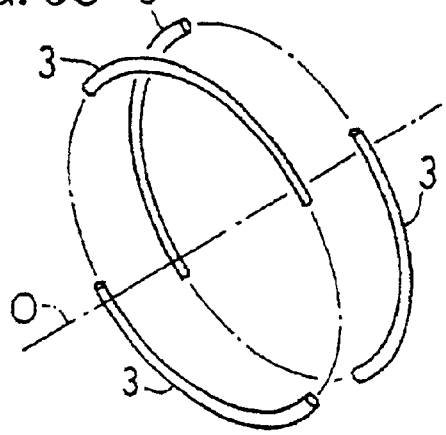
FIG. 3C is a schematic perspective view illustrating another example where a plurality of guides are provided so as to be spaced apart from each other in the axial direction of an axis O.

FIG. 3A to FIG. 3C schematically illustrate a third embodiment of the rotation device of the present invention.

The rotation device 1 illustrated in FIG. 3A includes an endless guide 3, a plurality of moving sections 4*i* moving along the guide 3, and the rotation section B. The rotation section B allows the guide 3 to rotate about the axis of the rotation section B.

The plurality of moving sections 4*i* are arranged in the rotation allowance direction of the section B (i.e., the direction in which the rotation section B allows the guide 3 to rotate). Each moving section 4*i* can move away from or toward an adjacent moving section 4*j*, and can reciprocate along the guide 3 in the direction of rotation of the rotation section B or in the opposite direction. If the reciprocating movement is done over a particular region of the rotation section B, the guide 3 may not need to be endless. Specifically, a plurality of arc-shaped guides 3 may be arranged about the axis O of the rotation section B so as to be spaced apart from one another in the rotation allowance direction of the rotation section B, surrounding the axis O. In such a case, each of the plurality of guides 3 includes at least one moving section that is movable in the direction of rotation of the rotation member or in the opposite direction.

The guide 3 of FIG. 3A is rotated at a predetermined rotational velocity about the axis O by a rotational force applying member (e.g., a motor or a power transmission device), which is not shown in the figure. The annular guide 3 is arranged at a predetermined position with respect to the rotation section B. A plurality of moving sections 4$_1$ to 4*i* are movably attached to the guide 3.

Each moving section 4*i* can move along the guide 3 along with the rotation of the rotation section B.

The interval between a pair of adjacent moving sections (e.g., 4$_2$ and 4$_3$) changes depending on the rotational position. A predetermined controller as described above may be employed to accurately control such an interval. However, a certain level of control can be provided by, for example, the gravitational acceleration acting on the moving sections 4*i*. Alternatively, a motor may be provided for each moving section 4*i* for driving the moving section 4*i* along the guide 3 so that the moving section 4*i* rotates at an instantaneous velocity according to a rotational angle $\theta_i$.

In the third embodiment, the rotation section B may be optional. The rotation device 1 includes the endless guide 3, and a plurality of moving sections 4*i* that move while being guided by the guide 3. The rotation device 1 in which the guide 3 is provided with a plurality of moving sections 4*i* may have a poor friction resistance as compared with one using ball bearings, but such a rotation device 1 can be lighter in weight than rotation devices in the prior art.

Figure 4:
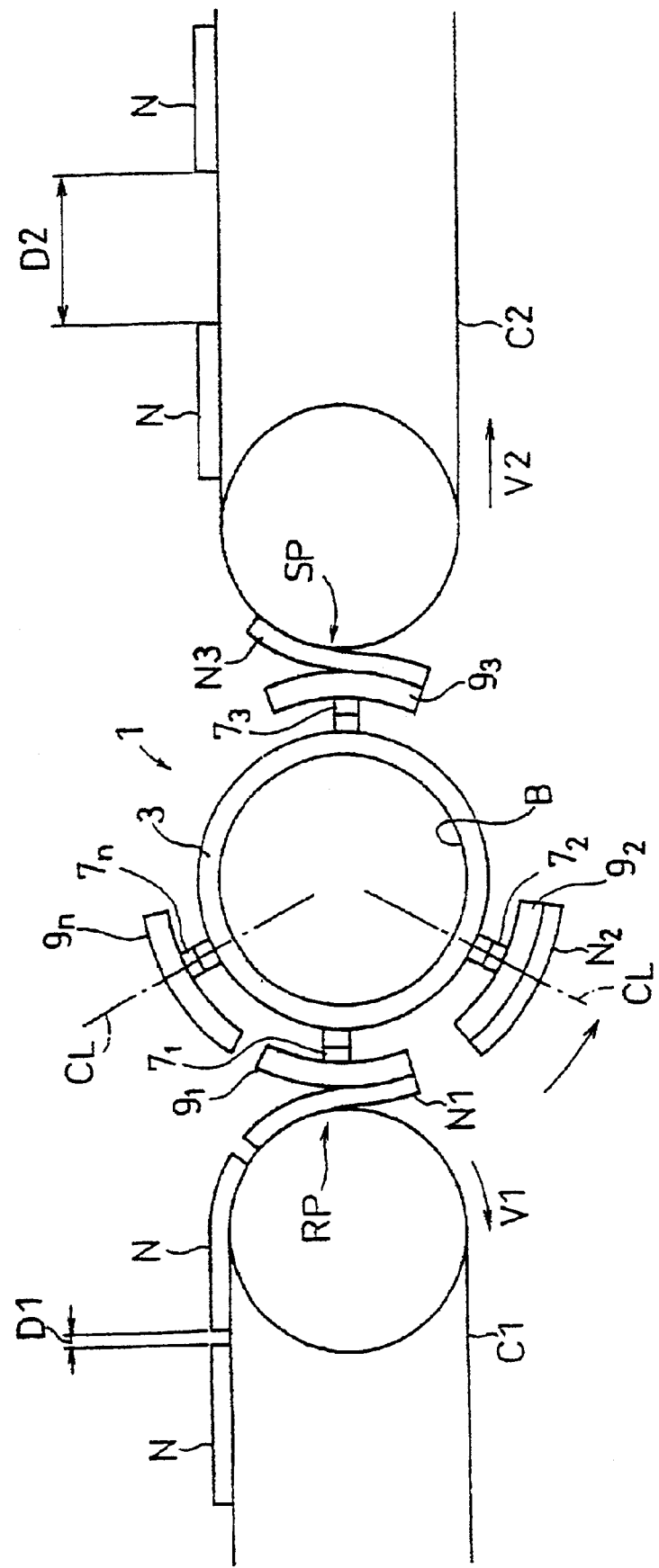
FIG. 4 is a schematic side view illustrating a transfer device.

FIG. 4 illustrates an example of a method for transferring a worn article using the rotation device 1.

The rotation device 1 includes pads 9*i* each attracting an article N and allowing the article N to be transferred. In the rotation device 1 illustrated in FIG. 1A and FIG. 1B, each pad 9*i* may be provided in the bridging section, or the bridging section may serve as a pad (i.e., the bridging section itself may be used as a pad). In the rotation device 1 illustrated in FIG. 2A and FIG. 2B, each pad 9*i* may be fit into the attachment section 75*i* of the bridging section so that the pad 9*i* can rotate (e.g., about the direction normal to the drum 6), or the bridging section may serve as a pad. In the rotation device 1 illustrated in FIG. 3A to FIG. 3C, each pad 9*i* may be provided in the moving section.

Each pad 9*i* of FIG. 4 includes a plurality of suction holes for attracting the article N, and the suction holes are placed under a negative pressure to attract the article N while the pad is moving from the position of the pad 9$_1$ (where the article N is received from a first conveyer C1) to the position of the pad 9$_3$ (where the article N is handed over to a second conveyer C2). The pad 9*i* may alternatively attract the article N by using an electrostatic charge, or the like.

The first conveyer C1 is provided upstream of the rotation device 1, and the second conveyer C2 is provided downstream of the rotation device 1. The first conveyer C1 transfers the articles N to the rotation device 1 at an interval D1.

For example, each pad 9*i* rotates at a circumferential velocity V1 that is about the same as that of the first conveyer C1 from when it comes near a pickup position RP until it passes the pickup position RP, and rotates at a circumferential velocity V2 that is about the same as that of the second conveyer C2 from when it comes near a hand-over position SP until it passes the hand-over position SP. In the rotation device 1 illustrated in FIG. 4, i.e., in a case where it is desired to increase the interval between pads, the relationship between the circumferential velocities is V2>V1. However, the relationship between the circumferential velocities is V2<V1 in a case where it is desired to shorten the interval between pads. The circumferential velocity of the second conveyer is about V2.

As the article $N_1$ is transferred by the first conveyer C1 to the pickup position RP, article $N_1$ is attracted onto the pad $9_1$ and the pad $9_1$ receives the article $N_1$ at the pickup position RP. Then, the pad $9_1$ rotates toward the hand-over position SP, where the pad $9_3$ releases the article $N_3$, while gradually increasing the velocity thereof. At the hand-over position SP, the pad $9_3$ stops attracting the article $N_3$, whereby the second conveyer C2 can easily attract and receive the article $N_3$.

In a case where a portion of the pad $9_i$ is rotatably fit into the attachment section of the bridging section, the pad $9_i$ may rotate about a normal direction CL by a predetermined angle (e.g., 90°) to change the orientation of the article $N_i$ while the pad $9_i$ moves from the pickup position RP to the hand-over position SP. The article $N_i$ may be a final or intermediate product of a worn article such as a napkin, a disposable diaper, disposable pants or a bandage, or may be a single-layer or multilayer sheet of woven fabric, non-woven fabric, a liquid permeable sheet or a liquid impermeable sheet. The intermediate product may be an absorbent or absorbents arranged over a web.

Figure 5:
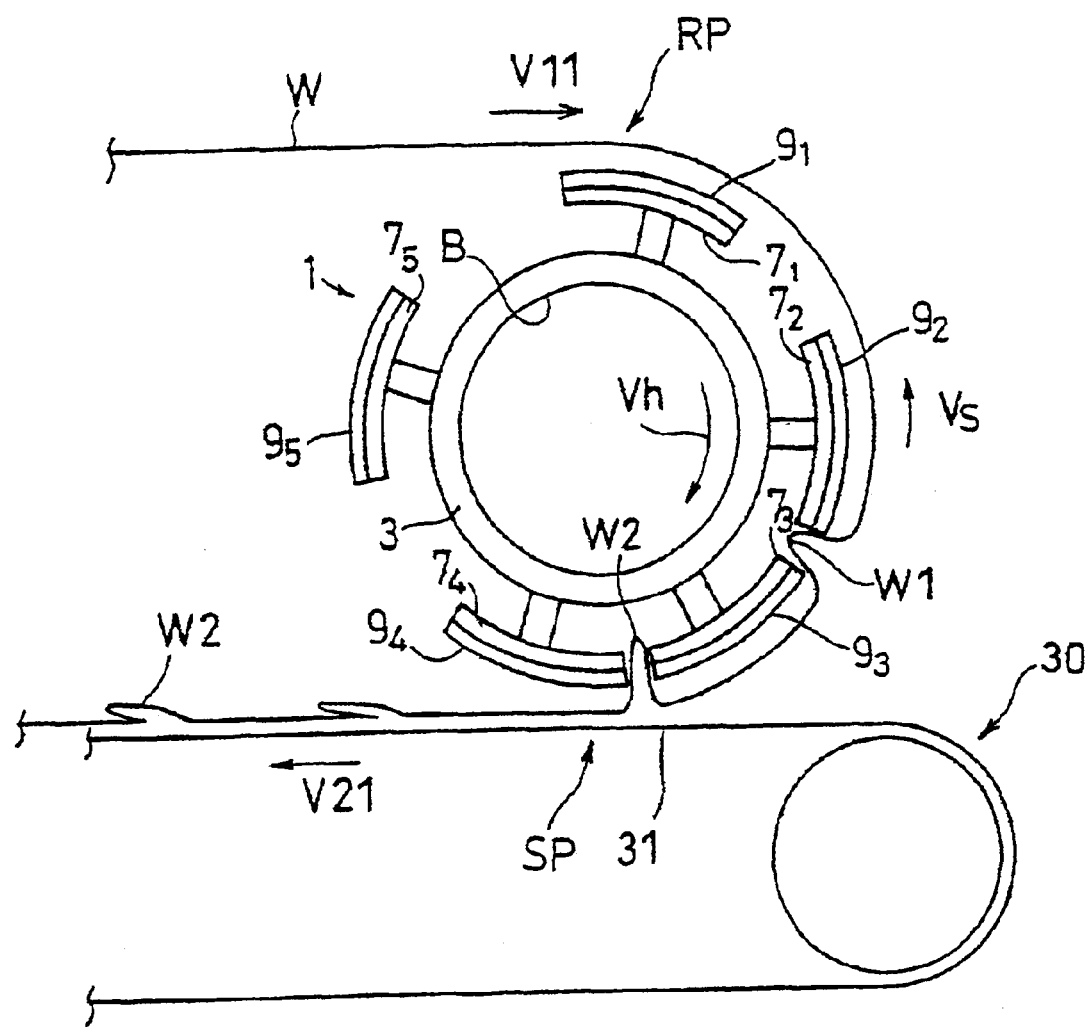
FIG. 5 is a schematic side view illustrating a folding device.

FIG. 5 illustrates an example of a method for folding a web W using the rotation device 1.

In the figure, each bridging section $7_i$ includes the pad $9_i$ for attracting the web W so that the web W can be transferred. The pad $9_i$ attracts the web W while it is moving from the position of the pad $9_1$ (where the web W is received) to the position of the pad $9_3$ (where a folded web is transferred) in FIG. 5.

The rotation device 1 forms a wheel for continuously transferring the web W, and is in contact with the surface of a belt 31 of a conveyer 30 via the web W.

The rotation device 1 picks up the web W traveling at a first velocity V11, and hands it over to the conveyer 30 traveling at a second velocity V21 (V11>V21). The belt 31 of the conveyer 30 basically transfers the web W at the circumferential velocity V21. Specifically, each pad $9_i$ rotates at the circumferential velocity V11 at the position of the pad $9_1$ (where the web W is received), and slows down to the circumferential velocity V21 by the time it reaches the position of the pad $9_3$ (where a folded web is transferred). Therefore, the interval between adjacent pads $9_i$ is shortened while the pads $9_i$ move from the pickup position RP to the hand-over position SP, thereby slackening the web W between the pads $9_i$ to form a slack portion W1.

Next, the operation will be described. The web W is supplied by being attracted onto the surface of the pad $9_1$ at the pickup position RP, and then transferred along the pads $9_i$ of the rotation device 1. While the rotation section B rotates in the direction of an arrow Vh, the pad $9_1$ moves along the guide 3 and in the opposite direction Vs, thereby reducing the interval between the pads $9_i$. The direction Vs is defined with respect to the guide 3. Therefore, a folded portion W2 is formed in the web W. After the formation of the folded portion W2, the pad $9_4$ stops attracting the web W, whereby the web W including folded portions W2 at a predetermined pitch is transferred onto the conveyer 30, thereby performing a so-called "Z-shaped folding process".

The rotation device for performing the Z-shaped folding process may not be the rotation device 1 described above, but may alternatively be, for example, a device described in PCT International Publication WO01/44086, or a device using any other link mechanism.

Figure 7A:
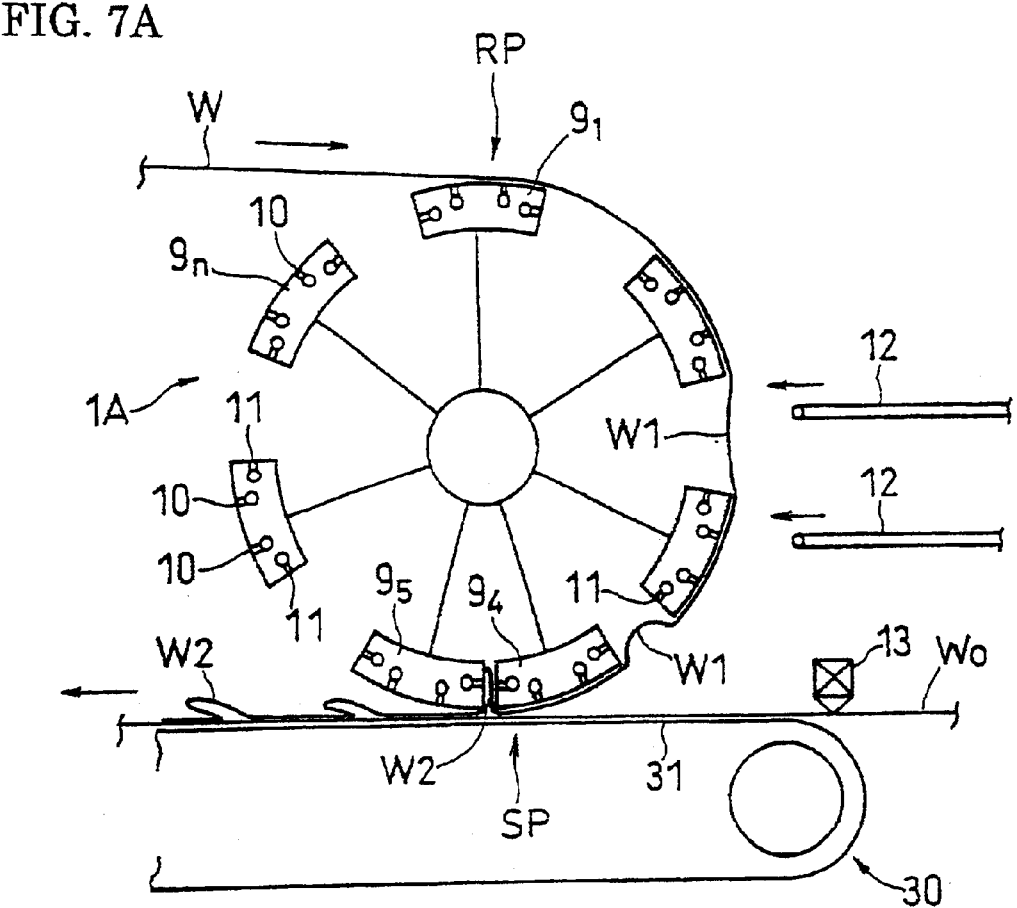
FIG. 7A is a schematic view illustrating a variation of a folding device.

Another example of a folding device for performing the Z-shaped folding process is illustrated in FIG. 7A.

In FIG. 7A a rotation device 1A includes a plurality of pads $9_i$. At least one suction hole 10 for attracting the web W is provided in the surface of each pad $9_i$. The velocity of the pad $9_i$ is the same as that of the web W at the pickup position RP. However, at the hand-over position SP, the velocity is lower than that at the pickup position RP. Therefore, a slack portion W1 is formed in the web W. Preferably, the folding device includes a directioning section 12 so as to ensure that the slack portion W1 is folded in toward the center of the rotation device 1A.

The directioning section 12 may be, for example, a mechanism that blows out a stream of air, a mechanism that thrusts the slack portion W1 of the web toward the center of the rotation device 1A, or a mechanism that sucks the web W toward the center of the rotation device 1A by a vacuum. Where the air blowing mechanism is employed, only one directioning section 12 may be provided, or a plurality of orientation sections 12 may alternatively be provided as illustrated in FIG. 7A. Also, where the slack portion thrusting mechanism is employed, only one directioning section 12 may be provided, or a plurality of orientation sections 12 may alternatively be provided. By providing a plurality of orientation sections 12, it is possible to reliably fold in the slack portion W1 toward the center of the rotation device 1A. The width of the directioning section 12 (the length thereof in the direction perpendicular to the surface of the sheet of the figure) can be set to a value (a length in the direction perpendicular to the surface of the sheet of the figure) according to the width of the web W.

Moreover, one or more suction holes 11 may be provided on each of the side surfaces of the pads $9_i$ by which the web W is to be sandwiched, i.e., on the side surfaces of each pad that face the side surfaces of the adjacent pads, so that the slack portions W1 of the web W are laid down along the side surfaces of the pads $9_i$.

The direction in which the web is to be folded may be the direction in which the web runs or the opposite direction. For example, in a case where the circumferential velocity of the trailing one of two pads that sandwich the web therebetween is higher than that of a conveyer in the vicinity of the hand-over position SP, the web is folded by the trailing pad in the running direction. In such a case, the leading pad is only required to move so as not to interfere with the movement of the trailing pad. In a case where the circumferential velocity of the conveyer is higher than that of the leading pad in the vicinity of the hand-over position SP, the web is folded by the leading pad in the direction opposite to the running direction.

In the present embodiment, a side surface of each pad $9_i$ in the circumferential direction forms a folded portion. Specifically, the side surfaces of two adjacent pads $9_4$ and $9_5$ that are facing each other in the circumferential direction come close to each other at the hand-over position SP so as to fold in two the web W therebetween, thereby forming the folded portion W2.

An applicator (an example of a fold-holding section) 13 for applying an adhesive such as a hot melt resin may be provided on the receiving side, as illustrated in FIG. 7A. The applicator 13 applies an adhesive on one or both of another web Wo and the web W to be folded so as to bond the webs Wo and W together, thereby making it easier to maintain the shape of the folded portion W2.

Figure 8:
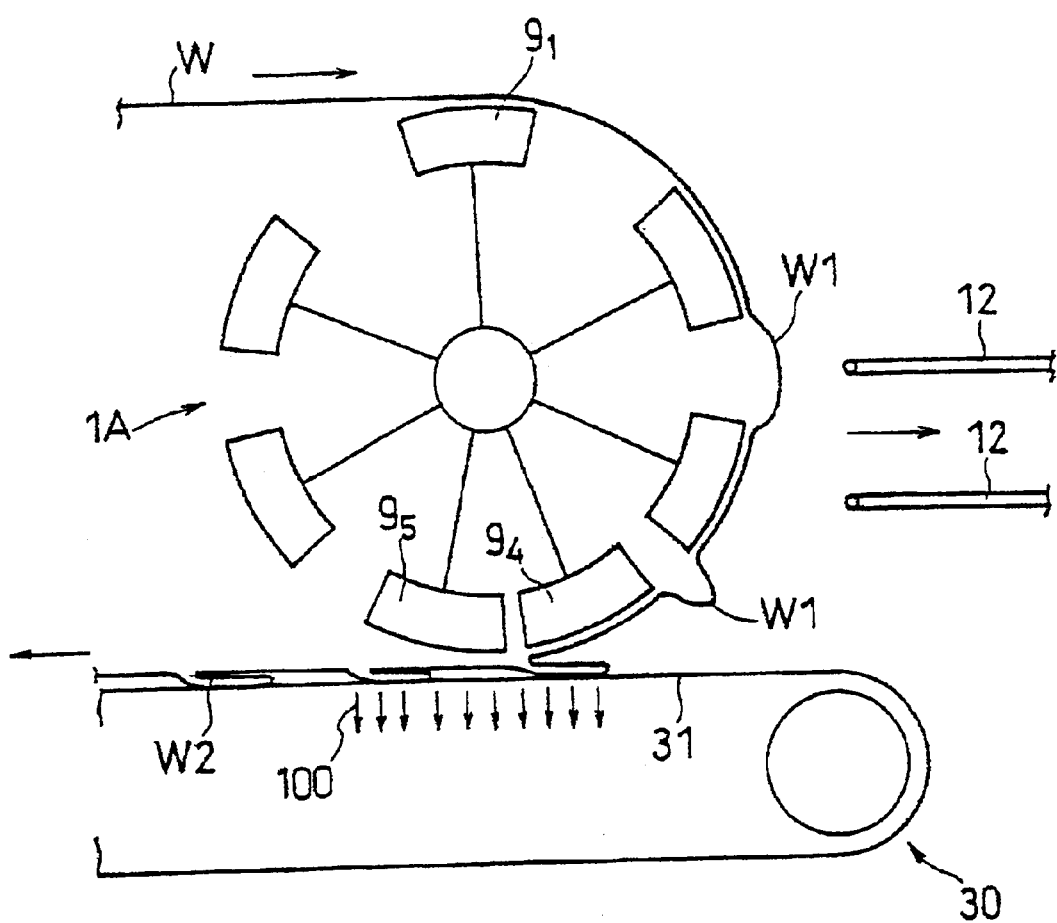
FIG. 8 is a schematic diagram illustrating another variation of a folding device.

Alternatively, in the present embodiment, a conveyer as illustrated in FIG. 8 may be used to maintain the shape of the folded portion W2.

Moreover, the directioning section 12 may suck in the slack portion W1 by a stream of air as illustrated in FIG. 8. The suction by the directioning section 12 forms the slack portion W1 into a shape that is protruding from the rotation device 1A. The suction of the web W, the number of the directioning sections, etc., may be set as those for the device of FIG. 7A.

Referring to FIG. 8, the slack portion W1 of the web is sandwiched between the pad $9_i$ and the belt 31 of the conveyer 30, thereby forming the folded portion W2. Another example of the fold-holding section provided on the receiving side may be, for example, a meshed belt 31 of the conveyer 30 capable of sucking an air therethrough by which the folded web W is received, wherein the web W is sucked by an air 100, as illustrated in FIG. 8, so as to maintain the shape of the folded portion W2. Instead of the meshed belt 31, a belt 31 including a plurality of holes therein may be used. Moreover, the fold-holding section may alternatively maintain the shape of the slack portion W1 by using an electrostatic charge, or the like.

Figure 7B:
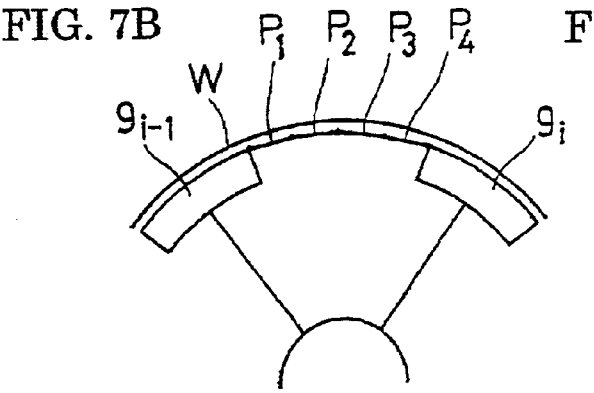
FIG. 7B is a diagram illustrating plates between two pads being in a spread formation.

A bellows-shaped folding device for performing a bellows-shaped folding process, which is a modified version of the Z-shaped folding process, will be described with reference to FIG. 7B to FIG. 7D. The bellows-shaped folding device is capable of folding the slackened web W at a plurality of positions.

The bellows-shaped folding device includes, in addition to the elements of the folding device of FIG. 7A, a plurality of plates $P_i$ between adjacent pads $9_{i-1}$ and $9_i$. As illustrated in FIG. 7D, the plates $P_i$ are pivotally connected to one another and to the pads $9_i$ via joints $J_i$. For example, the plate $P_1$ is pivotally connected to the pad $9_{i-1}$ via the joint $J_1$, and the adjacent plate $P_2$ is pivotally connected to the plate $P_1$ via the joint $J_2$.

Each plate $P_i$ is capable of sucking the web W. Each plate $P_i$ may include at least one suction hole, through which the web W is sucked. In such a case, each plate $P_i$ may be meshed. Moreover, the bellows-shaped folding device may have each plate $P_i$ charged with a first charge and the web with another charge that attracts the first charge, so as to attract the web W onto the plate $P_i$.

Figure 7C:
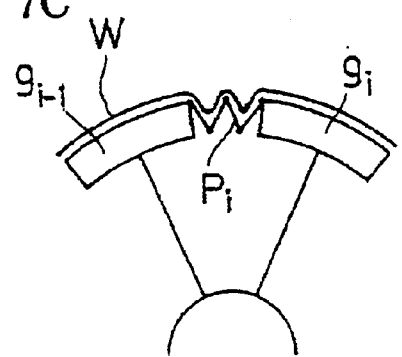
FIG. 7C is a diagram illustrating plates being folded into a bellows-like shape.
Figure 7D:
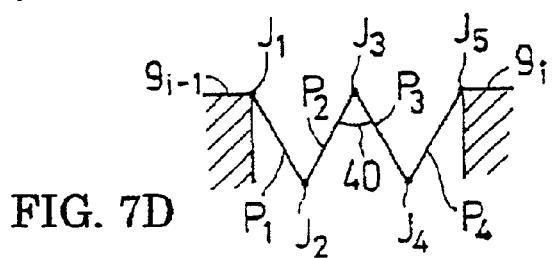
FIG. 7D is an enlarged view illustrating plates between two pads.

Referring to FIG. 7C, as the interval between adjacent pads $9_{i-1}$ and $9_i$ is shortened, the plurality of plates $P_i$ that have been in a spread formation are turned into a bellows-like shape. The joints $J_i$ between the plates $P_i$ may restrict the angle by which the connected plates $P_i$ can pivot in order to form a predetermined bellows-like shape in the web. For example, an elastic member 40 may be provided between the plates $P_2$ and $P_3$ as illustrated in FIG. 7D so as to restrict the angle by which the plates $P_i$ can pivot.

As the interval between adjacent pads $9_{i-1}$ and $9_i$ is shortened, the web W attracted onto the plates $P_i$ is bent so as to conform with the shape of the plates $P_i$. The slackened web W is folded so as to have top portions and bottom portions and is transferred onto the conveyer 30.

The folded web W may be transferred onto the conveyer 30 after the interval between adjacent pads $9_{i-1}$ and $9_i$ has been shortened and before the interval therebetween reaches its maximum value. In such a case, a triangular prism-shaped wall Tw is formed as illustrated, for example, in FIGS. 10 and 11.

Figure 9:
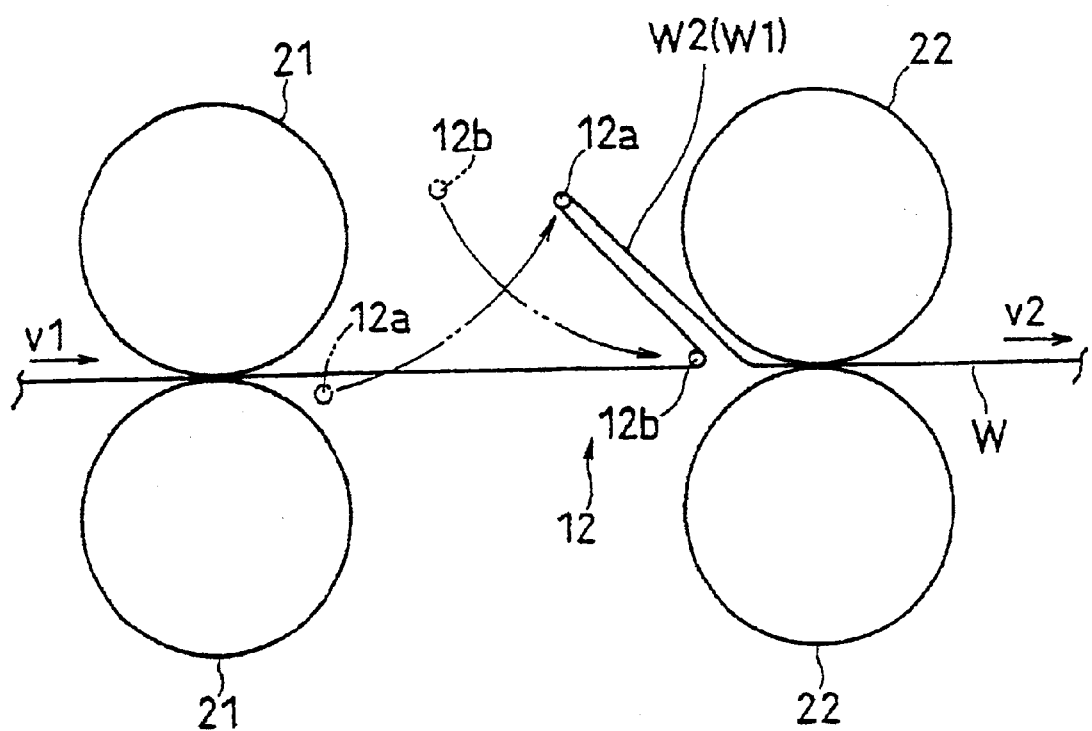
FIG. 9 is a schematic diagram illustrating another embodiment of a folding device.

FIG. 9 illustrates another example of a folding device. In the figure, a pair of first rolls 21 and 21 having a high transfer speed v1 are provided upstream, with respect to the transfer direction, along the web W, and a pair of second rolls 22 and 22 having a low transfer speed v2 are provided downstream along the web W.

Since the velocities satisfy v1>v2, the slack portion W1 is formed between the first rolls 21 and the second rolls 22. The direction in which the slack portion W1 is folded is determined by the directioning section 12. In the present embodiment, the directioning section 12 includes two bars 12a and 12b extending in the width direction of the web W. Broken lines in the figure represent the respective traces of the two bars. The second bar 12b moves after the first bar 12a moves, thereby forming the folded portion W2. Since the web W is made of a relatively light material such as non-woven fabric, pulp or a synthetic resin, the web W can easily be supported by the bars 12a and 12b with only one end thereof being fixedly supported. After the folded portion W2 is formed, the second bar 12b retracts toward the first rolls 21 before it is caught between the second rolls 22. Moreover, the first bar 12a can move in the width direction of the web W so as to extend beyond the edge of the folded portion W2.

It is possible to produce a disposable worn article, including a napkin, a diaper and pants, with a wall formed therein, by employing the "Z-shaped folding process" as described above.

Figure 10:
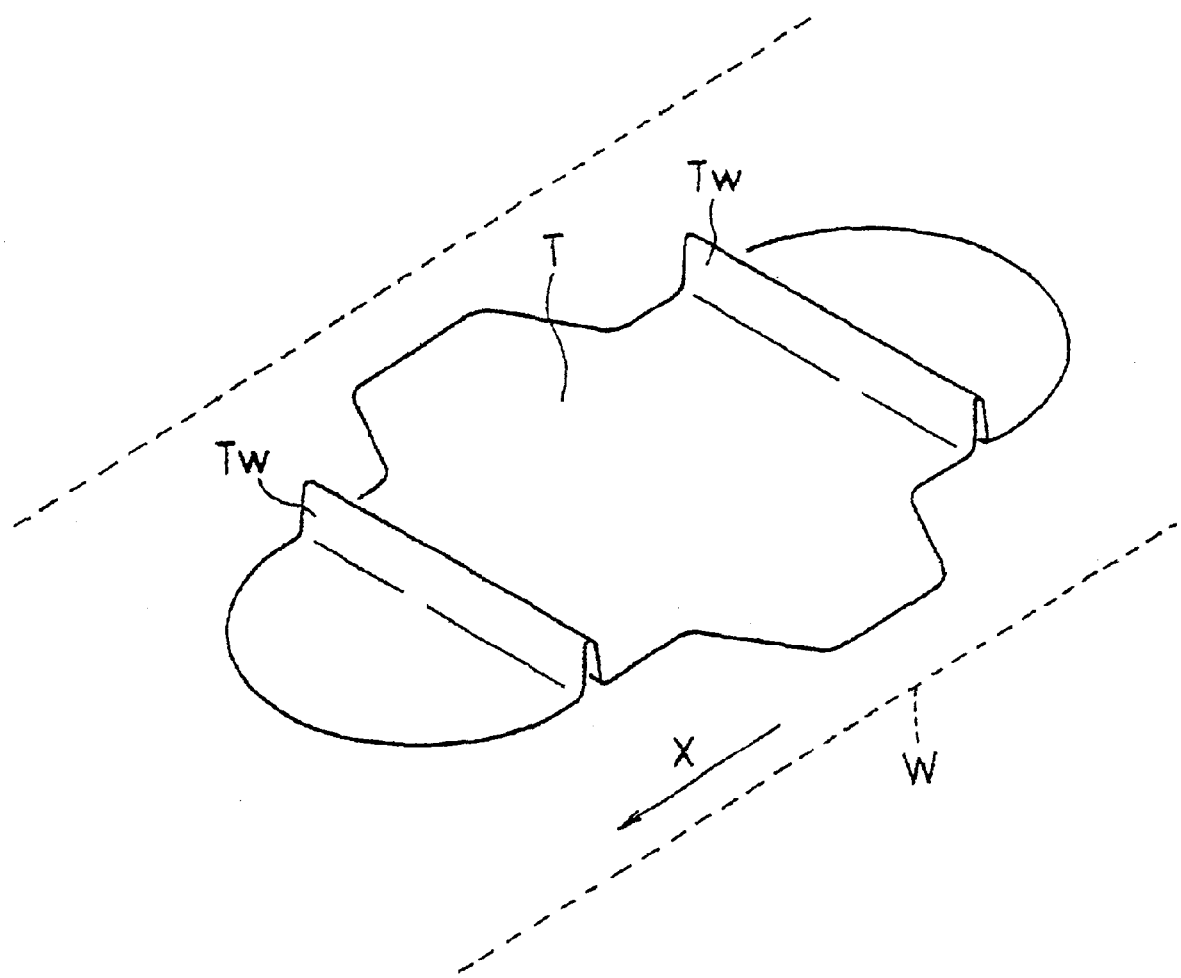
FIG. 10 is a perspective view illustrating an example of a top sheet.

FIG. 10 illustrates an example of a top sheet of a napkin, in which broken lines represent a web. In FIG. 10, the walls Tw are formed in a top sheet T so as to extend in a direction generally perpendicular to the running direction X of the top sheet T being produced. With the running direction X being a transverse direction, elongated walls Tw can be formed along the opposing sides of the napkin.

Figure 11:
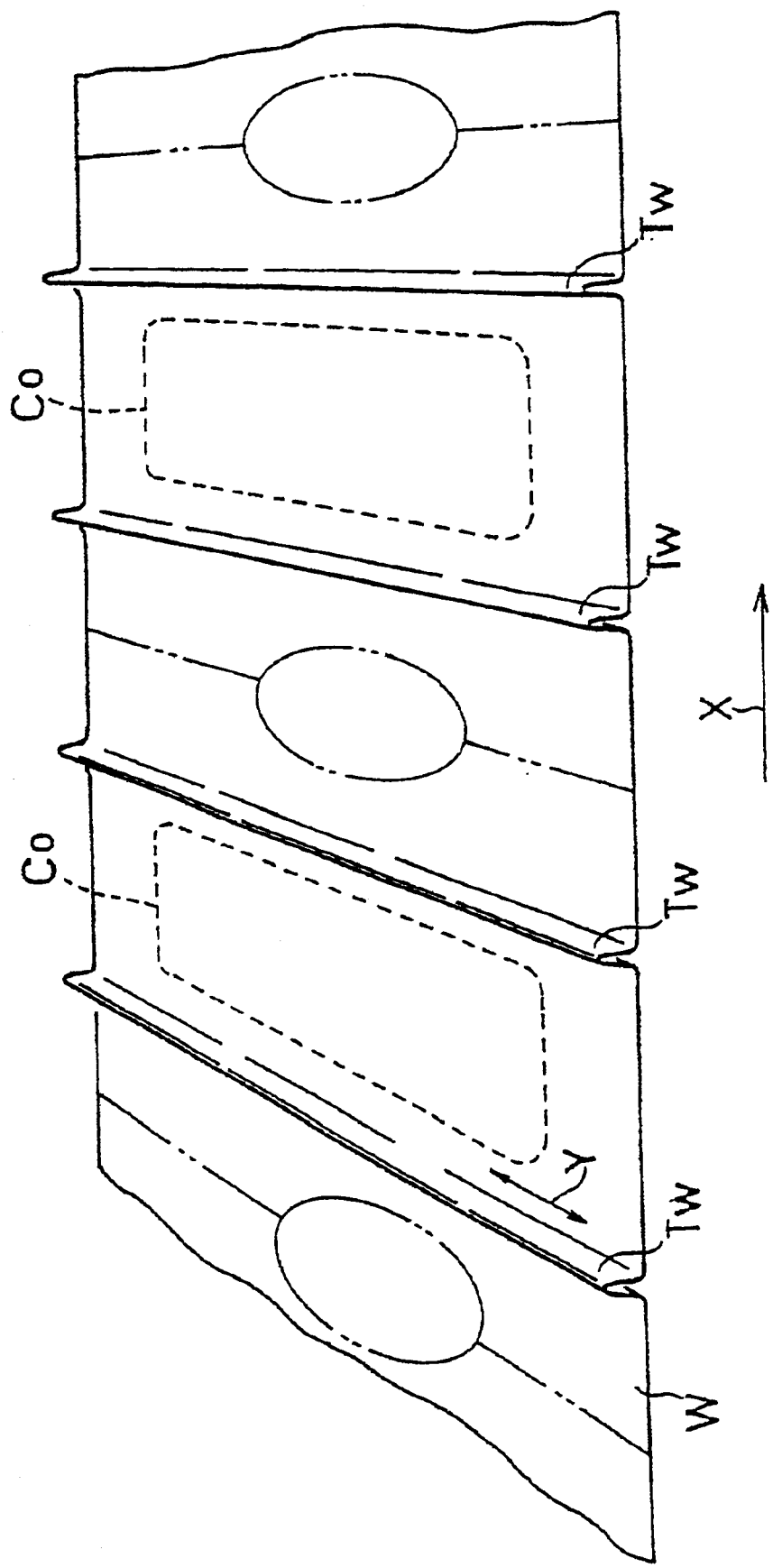
FIG. 11 is a perspective view illustrating an example of a top sheet before cutting.

FIG. 11 illustrates a top sheet (web) W of a diaper or pants before cutting. By slacking the web W using the folding method described above, the walls Tw can be formed in a direction Y transverse to a running direction X of the web W as illustrated in the figure. In other words, the longitudinal direction Y of the walls Tw is transverse to the running direction X of the web W. The longitudinal direction of an absorbent (core) Co denoted by a broken line is transverse to the running direction X of the web W (i.e., the production line is of a so-called "transverse flow" type). Therefore, it is possible to produce a diaper or pants in a transverse flow type production by cutting the web W in a direction transverse to the running direction (the X direction) as indicated by a two-dot chain line. As is well known in the art, a liquid impermeable back sheet, in addition to the absorbent Co, can be layered on the liquid permeable top sheet. The wall Tw may alternatively be formed on the absorbent Co. The wall Tw may be formed in the vicinity of an end of the absorbent Co, or a plurality of walls Tw may be formed in the vicinity of the end of the absorbent Co.

While the web is folded in a certain direction in the examples illustrated in FIG. 7A to FIG. 7D and FIG. 8, every other folded portion may be folded back in the opposite direction, for example, so as to form the walls Tw illustrated in FIG. 10 and FIG. 11.

An elastic member for making the worn article better fit to the wearer may be provided along the wall Tw. For example, a mechanism for attaching an elastic member that is extending in the direction Y transverse to the running direction X of the web W onto the web (e.g., a widening mechanism as described in Japanese Patent Application No. 12-028945) may be employed so as to provide an elastic member inside the wall Tw. The elastic member may be made of at least one flat or cord rubber.

The wall Tw of a disposable worn article such as a napkin, a diaper or pants as described above may be formed by the bellows-shaped folding process. Moreover, in a disposable worn article such as a napkin, a diaper or pants, a plurality of top portions and bottom portions may be formed on the absorbent Co through the bellows-shaped folding process. In such a case, excrement is drawn into the bottom portions, thereby reducing a leak from the worn article.

Figure 12:
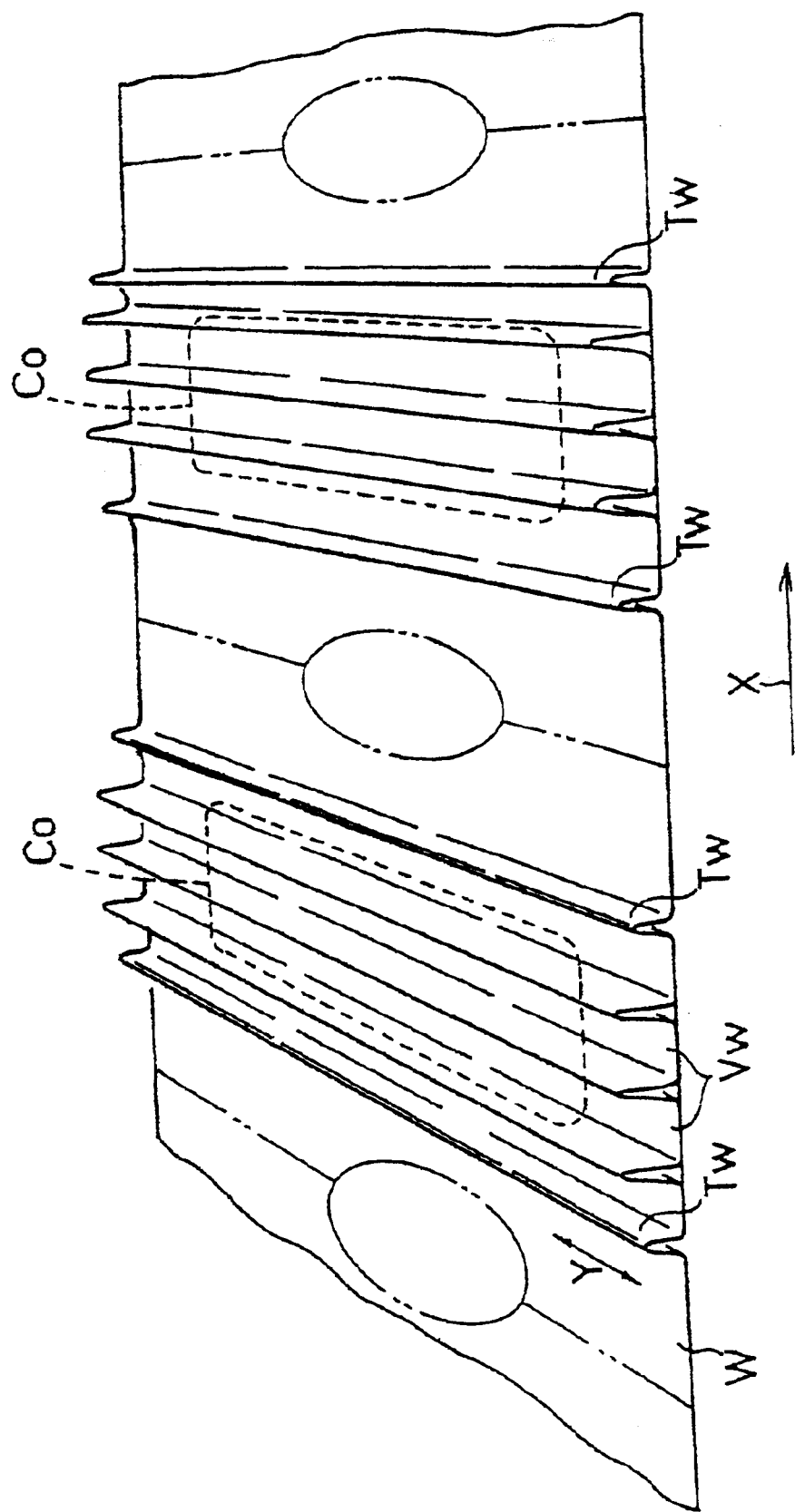
FIG. 12 is a perspective view illustrating another example of a top sheet before cutting.

FIG. 12 is a diagram illustrating an example of a plurality of walls Tw formed on each absorbent Co through the bellows-shaped folding process. The walls Tw may be positioned on the absorbent Co directly, or indirectly via a sheet, or the like. The sheet may be a continuous sheet, or at least one sheet may be layered between a plurality of walls Tw and an absorbent. In order to fix the walls Tw at predetermined positions, bottom portions Vw of the walls Tw are preferably flat. Specifically, the area over which the bottom portions Vw of the walls Tw contact the sheet or the absorbent Co is preferably 50% or more of the total area of the sheet or the absorbent Co.

Figure 13:
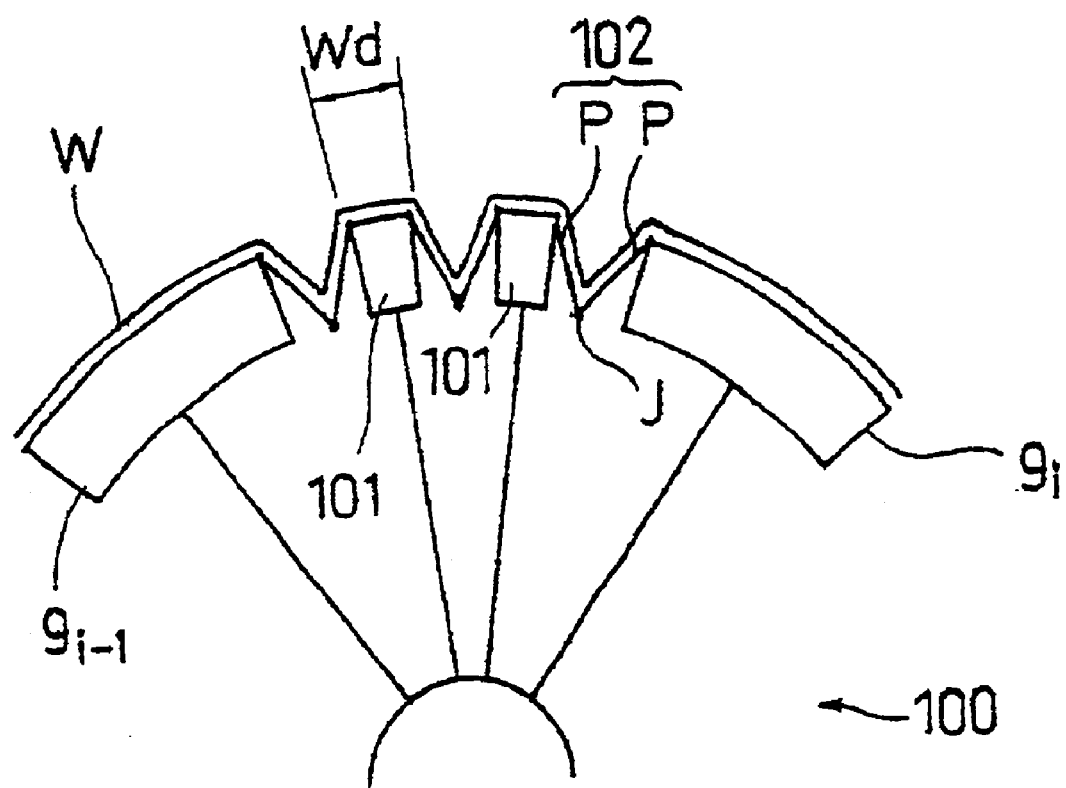
FIG. 13 is a diagram illustrating a portion of another example of a bellows-shaped folding device.

FIG. 13 is a diagram illustrating a portion of a bellows-shaped folding device 100 for forming bottom portions Vw that are generally flat. The bellows-shaped folding device 100 includes a plurality of pads $9_i$, at least one dummy pad 101, and a plurality of generally V-shaped plate pairs 102. Each of the generally V-shaped plate pairs 102 includes two plats P and P, and each plate P is capable of pivoting with respect to the other about the link between the plats P and P. One end of each generally V-shaped plate pair 102 is connected to the dummy pad 101 or the pad $9_i$.

At least one of the pads $9_i$, the dummy pad 101 and the generally V-shaped plate pair 102 is capable of sucking the web W onto the surface of the plats P and P and the surface of the top portion of the dummy pad 101. Where the width Wd of the bottom portion of the wall is 1 cm or less, the web W may be sucked by using only the pads $9_i$ and the generally V-shaped plate pairs 102. When the width Wd of the bottom portion of the wall is so small, the web W can be attracted and secured only by suction by the pads $9_i$ and the generally V-shaped plate pairs 102.

Preferably, the surface configuration of the pads $9_i$ and the dummy pads 101 is such that the surfaces of the pad $9_i$ and the dummy pad 101 contact the conveyer when handing over the folded web W to the conveyer.

Moreover, it is possible to attach at least one elastic member to a web in an intermittent manner by employing the "Z-shaped folding process". Accordingly, a disposable worn article including a web with at least one elastic member attached thereto in an intermittent manner can be produced by employing the "Z-shaped folding process".

Figure 14A:
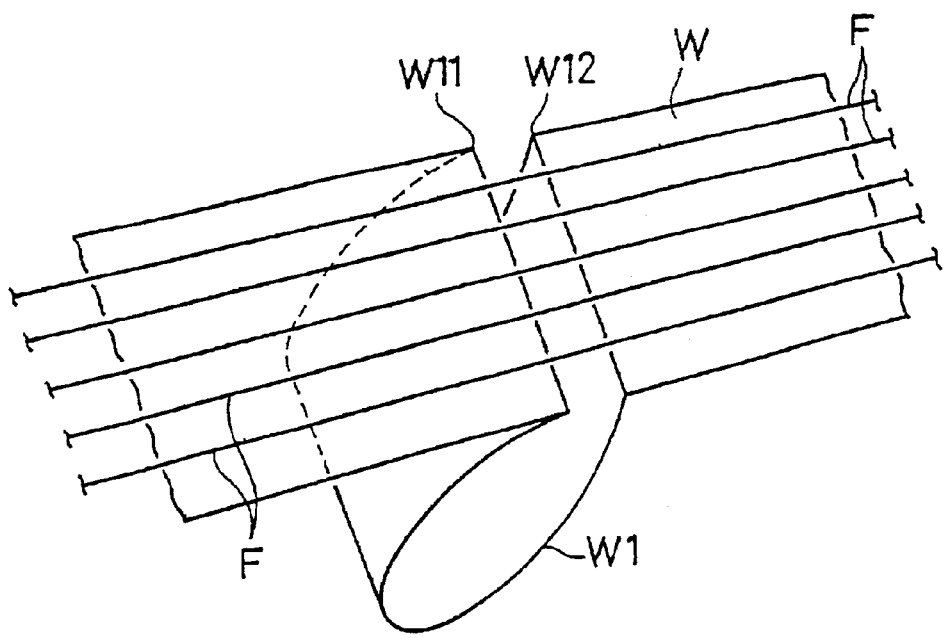
FIG. 14A is a diagram illustrating an elastic member being introduced so as to extend across a slack portion that has been obtained through a "Z-shaped folding process".

Specifically, at least one elastic member is bonded to a web, with a slack portion having been formed therein through the "Z-shaped folding process", so that the elastic member extends across the slack portion, as illustrated in FIG. 14A. Then, the elastic member F is cut off in the vicinity of a position between one edge W11 of the slack portion W1 of the web W and the other edge W12 of the slack portion W1. The elastic member F may be cut by using a straight cutter or an embossing roll. A straight cutter, an embossing roll, or the like, can cut off the elastic member through the application of heat, pressure, or a combination thereof, for example. U.S. patent application Ser. No. 09/891,034, PCT International Publication WO00/76444 and Japanese Laid-Open Patent Publication No. 2000-26015 are incorporated herein by reference, with respect to a cutting method using an embossing roll. Upon the cutting off of the elastic member, the slack of the web is eliminated.

Figure 14B:
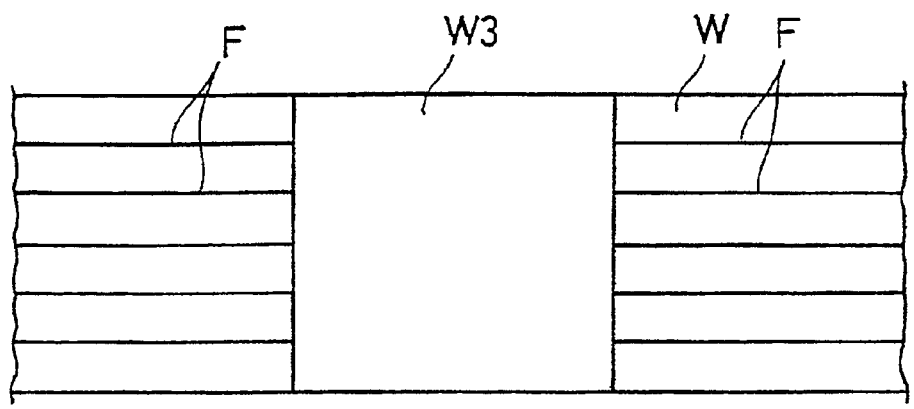
FIG. 14B is a diagram illustrating a web after cutting off the elastic member and removing the slack.

FIG. 14B is a diagram illustrating the web W after cutting off the elastic member F and eliminating the slack. In this way, the elastic member can be provided on the web W except for a portion W3 that has been a slack portion. Thus, it is possible to provide the web W with pieces of at least one elastic member F that are spaced apart from one another at a constant interval.

Figure 15:
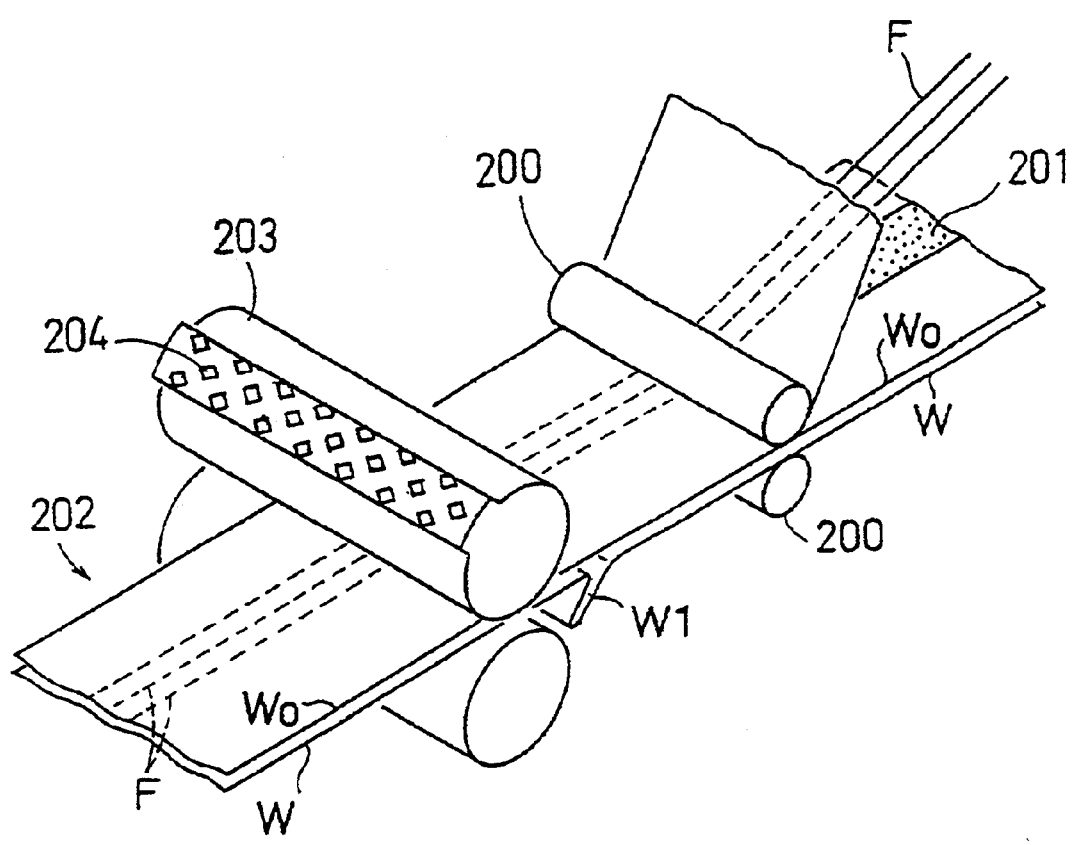
FIG. 15 is a diagram illustrating an example of a device for intermittently introducing an elastic member between a first web that has been subjected to a "Z-shaped folding process" and a second web.

An elastic member F may be sandwiched between a first web that has been subjected to the "Z-shaped folding process" and a second web. FIG. 15 illustrates an example of a device for intermittently introducing an elastic member F between a first web W that has been subjected to the "Z-shaped folding process" and a second web Wo.

The device applies an adhesive 201 on at least a portion of at least one of the first web and the second web. Then, nip rolls 200 secure the first web W, the elastic member F and the second web Wo with respect to one another. The laminate obtained by the nip rolls 200 is passed to an embossing roll 203. The embossing roll 203 is provided with a plurality of protrusions that cut off at least one the elastic member F of the laminate along with a portion of the second web Wo. The tip of each protrusion may be sharp as disclosed in U.S. patent application Ser. No. 09/891,034.

The second web Wo may be provided with a slit at each position corresponding to a slack portion W1 of the first web W. When the slack W1 of first web W is eliminated, i.e., when the laminate on which the elastic member F has been cut off is placed under a tension, the second web Wo is also cut off along the slit.

Alternatively, the second web Wo may include a slack portion. In such a case, the first web W, the elastic member F and the second web Wo are bonded together so that the position of the slack portion of the first web W corresponds to the position of the slack portion of the second web Wo. Only the elastic member F may be cut off. For example, it is possible to cut off only the elastic member F by employing an elastic member F whose melting point is lower than that of the second web Wo and embossing the laminate while heating the embossing roll 203 to a predetermined temperature. It is possible to cut off only the elastic member F with substantially no heat-induced alteration to the second web Wo if the temperature of the embossing roll 203 is higher than the melting point of the elastic member F and lower than the melting point of the second web Wo. Moreover, even when the temperature of the embossing roll 203 is higher than the melting point of the second web Wo, it is possible to cut off the elastic member before holes are created in the second web if the running velocity of the laminate is high.

Figure 16:
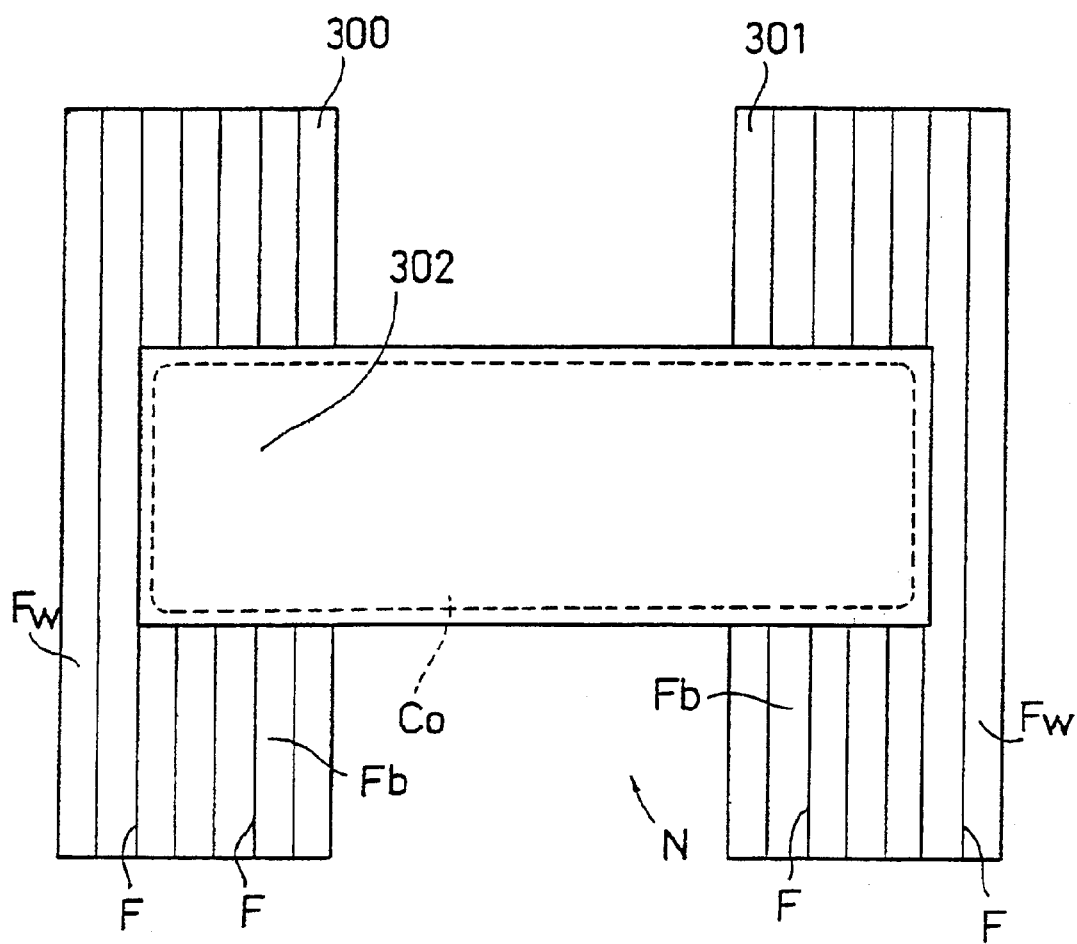
FIG. 16 is a diagram illustrating an example of a pants-shaped diaper, which is a disposable worn article, being spread out.

FIG. 16 is a diagram illustrating an example of a pants-shaped diaper N, which is a disposable worn article, being spread out. The pants-shaped diaper N includes an absorbent Co, a front flap 300 and a back flap 301. The front flap 300 and the back flap 301 include a waist gather Fw that closely fits to the wearer around the waist, and a fit gather Fb that fits to the abdominal part of the wearer. The fit gather Fb is generally absent in a portion where the pants-shaped diaper and the absorbent Co overlap with each other. If there is an elastic member F in the overlapped portion, the absorbent Co shrinks, thereby deteriorating the comfort to the wearer. The front or back flap 300, 301 can be produced by attaching an elastic member to a web in an intermittent manner by using the "Z-shaped folding process" described above. Note that the pants-shaped diaper may include a wall as described above. The worn article described above may of course be an article other than a pants-shaped diaper, such as a diaper with adhesive tapes.

The elastic member described above may be a polyurethane fiber, a natural rubber or a synthetic rubber, The polyurethane fiber may be LYCRA® manufactured by E I du Pont de Nemours and Company. The elastic member may be in the form of a cord, a string or a net, or have a flat shape. As a net-shaped elastic member, Rebound® manufactured by CONWED PLASTICS may be used.

As described above, in the rotation device of the present invention, rotation member is provided so as to allow a guide to rotate, with the guide being provided with a plurality of moving sections, whereby each moving section can slide independently. Therefore, the friction between the guide and the moving sections is significantly reduced, and thus it is possible to rotate the moving section continuously over a long period of time. Moreover, a plurality of moving sections can be provided without being spaced apart from one another in the axial direction, whereby the size of the device can be reduced.

Moreover, when a plurality of moving sections are provided in the axial direction with a bridging section extending between the moving sections, the bridging section is stabilized because the bridging section can then be supported at two positions.

Moreover, with the folding method or the folding device of the present invention, it is possible to easily and efficiently form a folded portion or a wall in a direction transverse to the direction in which the first web is transferred.

A worn article including a wall formed as described above has different characteristics from those of a worn article having a wall that is parallel to the direction in which the first web is transferred.

What is claimed is:

1. A rotation device, comprising:
   an endless guide;
   a rotation section for allowing the endless guide to rotate; and
   a plurality of moving sections that move while being guided by the guide, wherein a spacing interval between the moving sections changes as the moving sections move, and wherein the plurality of moving sections rotate by being guided by the guide.

2. A rotation device according to claim 1, further comprising a pad that moves along with one of the moving sections,
   wherein an orientation of the pad changes, as the one moving section moves.

3. A rotation device according to claim 1, wherein the endless guide is arranged so as to surround the rotation section.

4. A rotation device, comprising:
   a plurality of guides;
   a plurality of moving sections that move while being guided by the plurality of guides; and
   a rotation section for allowing the plurality of guides to rotate, wherein:
   each guide guides at least one moving section; and
   the plurality of guides are arranged so as to surround the rotation section.

5. A rotation device according to claim 4, further comprising a pad that moves along with one of the moving sections,
   wherein an orientation of the pad changes as the one moving section rotates.

6. A rotation device, comprising:
   an endless guide comprising a plurality of guides;
   a plurality of moving sections that move while being guided by the guide; wherein a spacing interval between the moving sections changes as the moving sections move; and wherein the plurality of moving sections are provided in a rotation axis direction of a rotation section which allows the plurality of guides to rotate; and
   a bridging section attached between more than one of the moving sections provided in the rotation axis direction.

7. A rotation device according to claim 6, wherein:
   a the plurality of guides and the plurality of moving sections are provided in a rotation axis direction of the rotation section; and
   the rotation device further comprises a bridging section attached between more than one of the moving sections provided in the rotation axis direction.

8. A rotation device according to claim 6, further comprising a pad that moves along with one of the moving sections,
   wherein an orientation of the pad changes as the one moving section moves.

9. A rotation device according to claim 6, wherein the guides are arranged so as to surround the rotation section.

* * * * *